(12) United States Patent
Szewczyk et al.

(10) Patent No.: US 10,426,720 B2
(45) Date of Patent: Oct. 1, 2019

(54) FILM COMPOSITIONS FOR ORAL USE

(71) Applicant: COLGATE-PALMOLIVE COMPANY, New York, NY (US)

(72) Inventors: Gregory Szewczyk, Flemington, NJ (US); Nihal Dogu, Dayton, NJ (US); Suzanne Jogun, Wayne, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/107,590

(22) PCT Filed: Dec. 23, 2013

(86) PCT No.: PCT/US2013/077377
§ 371 (c)(1),
(2) Date: Jun. 23, 2016

(87) PCT Pub. No.: WO2015/099640
PCT Pub. Date: Jul. 2, 2015

(65) Prior Publication Data
US 2016/0317422 A1    Nov. 3, 2016

(51) Int. Cl.
| | | |
|---|---|---|
| *A61K 8/25* | (2006.01) | |
| *A61K 8/11* | (2006.01) | |
| *A61K 9/70* | (2006.01) | |
| *A61Q 11/00* | (2006.01) | |
| *A61K 8/73* | (2006.01) | |
| *A61K 9/00* | (2006.01) | |
| *A61K 8/02* | (2006.01) | |
| *A61K 8/34* | (2006.01) | |
| *A61K 8/44* | (2006.01) | |

(52) U.S. Cl.
CPC ............ *A61K 8/731* (2013.01); *A61K 8/0254* (2013.01); *A61K 8/25* (2013.01); *A61K 8/345* (2013.01); *A61K 8/44* (2013.01); *A61K 9/006* (2013.01); *A61Q 11/00* (2013.01); *A61K 2800/262* (2013.01); *A61K 2800/43* (2013.01); *A61K 2800/52* (2013.01)

(58) Field of Classification Search
CPC ...... A61K 8/731; A61K 2800/43; A61K 8/25; A61K 8/11; A61K 9/7007; A61Q 11/00
See application file for complete search history.

(56) References Cited

U.S. PATENT DOCUMENTS

| | | | |
|---|---|---|---|
| 3,662,059 A | 5/1972 | Wiesner et al. | |
| 3,935,306 A * | 1/1976 | Roberts | A61K 8/0275 424/49 |
| 6,136,297 A | 10/2000 | Sagel et al. | |
| 6,479,036 B1 | 11/2002 | Stanier et al. | |
| 6,669,229 B2 | 12/2003 | Thomas | |
| 7,763,235 B2 | 7/2010 | Boyd et al. | |
| 8,647,648 B2 | 2/2014 | Wang | |
| 9,138,384 B2 | 9/2015 | Boyd | |
| 9,522,111 B2 | 12/2016 | Szewczyk et al. | |
| 2002/0034479 A1 | 3/2002 | Green | |
| 2003/0095931 A1 | 5/2003 | Stier | |
| 2003/0099692 A1 | 5/2003 | Puglisi | |
| 2004/0136924 A1 | 7/2004 | Boyd et al. | |
| 2004/0247646 A1 | 12/2004 | Ivory et al. | |
| 2005/0019273 A1 | 1/2005 | Boyd et al. | |
| 2006/0134020 A1 | 6/2006 | Robinson et al. | |
| 2007/0020201 A1 | 1/2007 | Boyd et al. | |
| 2007/0122455 A1 | 5/2007 | Myers et al. | |
| 2007/0148213 A1 | 6/2007 | Ibrahim et al. | |
| 2007/0264487 A1 | 11/2007 | Georgiades | |
| 2008/0138369 A1 | 6/2008 | Boyd et al. | |
| 2008/0187497 A1 | 8/2008 | Agarwal et al. | |
| 2008/0187498 A1 | 8/2008 | Francis | |
| 2008/0245678 A1 | 10/2008 | Gantenberg | |
| 2008/0247967 A1 | 10/2008 | Sagel | |
| 2008/0247968 A1 | 10/2008 | Sagel | |
| 2008/0247969 A1 | 10/2008 | Glandorf | |
| 2008/0248072 A1 | 10/2008 | Glandorf | |
| 2008/0248073 A1 | 10/2008 | Gantenberg | |
| 2009/0060597 A1 | 3/2009 | Yoshida et al. | |
| 2011/0150954 A1* | 6/2011 | Lapidot | A61K 8/0241 424/401 |
| 2016/0324753 A1* | 11/2016 | Szewczyk | A61K 8/345 |

FOREIGN PATENT DOCUMENTS

| | | | |
|---|---|---|---|
| EP | 0255210 | 2/1988 | |
| EP | 1891937 A1 | 2/2008 | |
| EP | 2105122 | 9/2009 | |
| EP | 2116219 | 11/2009 | |
| EP | 1843738 | 3/2010 | |
| WO | WO 0042992 A2 * | 7/2000 | ............ A61K 9/0007 |
| WO | WO 03/015748 | 2/2003 | |
| WO | WO 03025748 A2 | 3/2003 | |
| WO | WO 2009/006218 A2 | 1/2009 | |
| WO | WO 2012002945 A1 * | 1/2012 | ............ A61K 8/02 |
| WO | WO 2012053006 A2 * | 4/2012 | ............ A61K 9/0056 |
| WO | WO 2012082103 A1 * | 6/2012 | ............ A61K 8/731 |
| WO | WO-2012087328 A1 * | 6/2012 | ............ A61K 8/02 |

OTHER PUBLICATIONS

Corresponding International Search Report and Written Opinion for PCT/US2013/077377 dated Apr. 15, 2014.

* cited by examiner

*Primary Examiner* — Tracy Liu

(57) ABSTRACT

Described herein are oral compositions comprising a film, wherein the film comprises a dye entrapped in a silica sol-gel.

15 Claims, No Drawings

FILM COMPOSITIONS FOR ORAL USE

CROSS-REFERENCE TO RELATED PATENT APPLICATIONS

The present application is a U.S. national stage application under 35 U.S.C. § 371 of PCT Application No. PCT/US2013/077377, filed Dec. 23, 2013, the entirety of which is incorporated herein by reference.

BACKGROUND

Using pigments within a polymer film in toothpaste is a technology used in markets outside of the US. In the US, however, only dye is allowed in oral care products. A significant problem of using water soluble dye is that the dye is water soluble and leaches out of a film almost immediately upon addition to a formulation that contains water, causing an unacceptable color bleeding.

There is a need for dentifrices, such as toothpastes, comprising films which contain a dye, such that the dye does not appreciably leach out from the polymer film until use.

SUMMARY

It has been discovered that when a dye is entrapped in a silica sol-gel and incorporated into a polymer film that is in turn incorporated into an orally acceptable carrier vehicle, the dye does not substantially leach from the film into the carrier vehicle until use i.e., when diluted with saliva and/or subjected to mechanical forces such as brushing. The compositions of the invention are oral care compositions can be color-changing films, which are attractive and stable in the formulation and provide a color change signal after a sufficient period of use. The oral compositions of the invention are stable upon storage, e.g., the dye does not substantially leach, migrate or leak from the film into the carrier vehicle during storage, but is released upon introduction into the oral cavity which, in some embodiments, provides a visible signal upon use.

In one embodiment the compositions comprise films comprising a high concentration of sol-gel/dye material, which are stable in formulation, but are adapted to provide a color change after a sufficient period of brushing. The user would be instructed to continue brushing until the color change was observed, to help ensure that they have brushed for a sufficient period of time.

In accordance with the present invention there is provided an oral care composition such as a dentifrice comprising:
(i) flakes of a water dissolvable or soluble film (hereinafter sometimes referred to as "film flakes") comprised of
  (a) a water soluble cellulose ether polymer and polyvinyl acetate in the form of a polymer matrix, and
  (b) a silica sol-gel the material entrained in the polymer matrix, and optionally, other actives, and
(ii) an orally acceptable carrier vehicle,
wherein the film flakes are pliable and preferably comprise betaine.

In one embodiment of the invention there is provided an aesthetically decorative dentifrice having distributed throughout film flakes in which a decorative silica sol-gel/dye material is entrained in the film matrix, the dentifrice vehicle being substantially clear so that the aesthetically decorative effect can be viewed by the user.

In another embodiment other actives such as therapeutic and/or cosmetic agents, in addition to the silica sol-gel/dye material, are entrained in the film polymer matrix and/or the orally acceptable carrier vehicle.

The entrainment of silica sol-gel/dye material and, optionally, other therapeutic and cosmetic agents in the film flake matrix suspended in the orally acceptable carrier vehicle isolates these agents from interaction with reactive ingredients present in the orally acceptable carrier vehicle so that the film flake agents are maintained substantially separate from the reactive dentifrice ingredients in the orally acceptable carrier vehicle during manufacture and storage while subsequently being released from the film matrix when the dentifrice containing the film flakes is topically applied to the tooth surface as by tooth brushing. The other ingredients can be, for example, fragrance, flavor, topical anesthetic, or topical antibacterial agent.

Some embodiments of the present invention further provide a composition which is subjected to agitation and moisture during use, e.g., an oral care product which is applied by brushing or scrubbing, for example a toothpaste.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

Silica Sol-gel Material

The silica sol-gel/dye material comprises a dye entrapped or encapsulated into a silica sol-gel. Such materials can be made by techniques known in the art, for example as disclosed in WO 2005/028604, WO 2004/081222, U.S. Pat. No. 6,074,629, U.S. Pat. No. 6,495,352, and US 2013/0091637 incorporated herein by reference.

Silica sol-gels refer to silicon dioxide based materials made through a sol-gel process.

Sols are formed first, which consist of a colloidal solution of very small (nanometer sized) polysiloxane particles formed through hydrolysis of the silane starting materials. Further polymerization/chemical reaction/hydrolysis converts the sols into gels by chemically linking together the individual colloidal sol particles into monolithic gels.

The sol-gel process involves low-temperature hydrolysis of suitable monomeric precursors and is suitable for encapsulation of dyes. The sol is usually formed by hydrolysis of an alkoxy silane precursor followed by condensation to yield a polymeric oxo-bridged $SiO_2$ network, hi the process, molecules of the corresponding, alcohol are liberated.

A sol can also be formed by the neutralization of an alkali metal salt of a silicate or organosiliconate with an acid.

In one embodiment a silica sol-gel matrix/dye is prepared by forming a silica sol from a solution of a silicon oxide and alkali metal oxide, such as potassium oxide or sodium oxide, in water, adjusting the pH to a pH value less than approximately 7 to stabilize the silica sol, forming a silica sol matrix solution, adding a solution containing a dye to be entrapped or encapsulated to form a silica sol matrix with entrapped dye, aging said silica sol matrix with entrapped dye, and forming a gel material.

In another embodiment a water-soluble dye to be encapsulated is dissolved in a prepared SiOx sol without using any further additives such as immobilizing or complexing agents. The dyed sol is subjected to a spray-drying process for gelling. Any solvent residues possibly present are removed by secondary drying. Starting materials suitable for the production of the spray-dried sol-gels are alkoxysilane sols which are produced from unsubstituted organosilicon compounds by hydrolysis, preferably heterogeneous catalysis. Tetraethoxysilane is a preferred starting material for the production of the alkoxysilane sol. Hydrolysis of the aqueous-organic alkali silicate solutions is effected at weakly acidic pH values, preferably at pH values of 5.0 to 6.5, particularly at pH values of 5.5 to 6.0. Acidification can be effected by careful addition of acids. Hydrolysis can be effected in the form of a heterogeneous catalysis, preferably with addition of acidic ion exchangers.

The Film

The films of the present invention are formed from film forming polymers in the form of a polymer matrix comprised of a cellulose polymer in Which is entrained a silica sol-gel/dye material, and, optionally other agents such as a flavorant, a sweetener and/or a therapeutic agent such as an antibacterial agent or a breath freshening agent. The film matrix can further comprise water, additional film forming agents such as corn starch, e.g., Hi-Set C™ from National Starch, or polyvinyl acetate; plasticizing agents, e.g., propylene glycol; surfactants comprising betaine; and emulsifying agents. The films of the invention are preferable single layer and pliable. By the term "pliable" is meant that the film will not easily tear nor crack during normal manufacturing and handling.

Cocamidopropyl Betaine

Cocamidopropyl betaine (sometimes referred to herein simply as "betaine") is an organic compound derived from coconut oil and dimethylaminopropylamine. It is a zwitterion, consisting of both a quaternary ammonium cation and a carboxylate. Betaine is available as viscous pale yellow solution that is used as a surfactant. The name reflects that the major part of the molecule, the lauric acid group, is derived from coconut oil. Cocamidopropyl betaine cart be viewed as the combination of cocamide and glycine betaine. It is however prepared by combining chloroacetic acid with the amide derived from dimethylaminopropylamine and lauric acid.

It has been surprisingly discovered that when the film of the invention containing the silica sol-gel/dye material also contains betaine as part or all of the surfactant, such film is pliable, whereas if a conventional surfactant, such as Tween 80, is used alone in forming the polymer film, such film is brittle. Even when the amount of plasticizer, such as propylene glycol, is increased, the resulting film is still brittle if the only surfactant used is Tween 80, Therefore, it is preferred that the surfactant used for film formation comprises betaine.

Preparation of Film Matrix

In preparing the film matrix according to the present invention the hydroxyalkyl cellulose, polyvinyl acetate, silica sol-gel/dye material, and, optionally, flavor sweetener and/or therapeutic agents and other film forming ingredients such as surfactant and plasticizer are dissolved in a compatible solvent to form a film forming composition. Compatible solvents include water, alcohols such as ethanol, ethyl acetate, acetone, and mixtures thereof. The film forming composition is cast on a releasable carrier and dried to form a sheet of film matrix material. The carrier material must have a surface tension which allows the film solution to spread evenly across the intended carrier width without soaking to form a destructive bond between the film carrier substrates. Examples of suitable carrier materials include glass, stainless steel. Teflon and polyethylene-impregnated paper. Drying of the film may be carried out at high temperature using a drying oven, drying terminal, vacuum drier, or any other suitable drying equipment which does not adversely affect the ingredients of which the film is composed.

The film thickness ranges in size from about 1 to 10 mils, in one embodiment about 1 to 5 mils, in another embodiment about 2 to 4 mils. The dried film of the present invention is then cut, punched or ground into flakes having a particle size of 10 to 100 mesh or 20 to 60 mesh or 30 to 50 mesh.

If desired, additional stability can be provided to the shapes formed from the dried film, by applying to the film, before shaping into flakes, a protective barrier overcoat such as a food grade shellac or ethyl cellulose.

When the film is to be used for decorative effect, the film once formed is punched into various attractive shaped flakes such as hearts, stars, diamonds and circles. Optionally, the film can be ground into flakes using conventional grinding techniques known in the art. The film flakes are incorporated in the orally acceptable carrier vehicle of the present invention at a concentration of about 0.05 to 1.0% by weight and in one embodiment about 0.1 to about 0.5% by weight.

Film Forming Polymers

The film forming polymer comprises a cellulose polymer, in particular cellulose ethers, e.g., selected from alkylcellulose, e.g., methylcellulose; hydroxyalkyl cellulose, e.g., selected horn hydroxypropyl methyl cellulose, hydroxyethylpropyl cellulose, hydroxy butyl methyl cellulose, hydroxy propyl methyl cellulose, carboxymethyl cellulose; and mixtures thereof. A preferred film forming polymer is hydroxypropylmethyl cellulose (HPMC). Preferably the cellulose ether polymer is a low viscosity hydropropylmethyl cellulose. The cellulose ether is incorporated in the film matrix in amounts ranging from about 10 to about 60% by weight and in one embodiment about 15 to about 40% by weight. Other film forming polymers may also be used in addition to the cellulose ether, for example, polyvinyl acetate, starch, e.g., a pregelatinized starch, and the like. HPMC is available commercially, for example, from the Dow Chemical Company under the trade designation Methocel™, including, for example, Methocel™ E5LV, Methocel™ E50, and Methocel™ K100. Methocel™ E5 LV is a USP grade, low viscosity HPMC having 28 to 30 (29.1) % methoxyl groups and 7 to 12 (9) % hydroxypropyl group substitution. As used herein, hydroxypropylmethylcellulose E5 refers to hydroxypropylmethylcellulose have a viscosity of about 5 (4 to 6) mPas (cps), and hydroxypropylmethylcellulose E50 refers to hydroxypropylmethyl cellulose have a viscosity of about 50 (40 to 60) mPas (cps). The viscosity for the hydroxypropylemethyl cellulose is measured in a 2 weight % solution in water at 20° C. with a Ubbelohde tube viscometer.

It is an advantage of the composition of the invention that the film does not require a polymer that functions as a mucoadhesive polymer, e.g., polymers containing acrylate repeating units such as Carbopol® polymers. The film of the invention also does not require starch, although it can be present in some embodiments.

The film flakes typically comprises about 0.01 to 5%, more typically about 0.015 to 5%, more particularly about 0.015 to 3% of the oral composition of the invention.

Dye

Preferred dyes are water soluble dyes. The term "water-soluble" in this particular context generally means that the dye has an aqueous solubility of at least 10 g/L at 25.degree, C., most preferably at least 100 g/L at 25° C. (where the solubility is determined in un-buffered distilled water). Triarylmethane dyes are examples of water soluble dyes useful in the present invention. In some embodiments, dyes useful herein are anionic triphenylmethane dyes, and especially diaminotriphenylmethane dyes containing from two to four sulphonate groups, such as those corresponding to general formula (1):

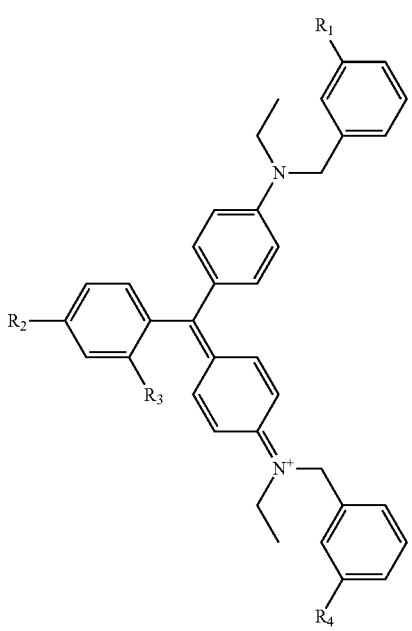

in which $R_1$, $R_2$, $R_3$ and $R_4$ are monovalent moieties which are each independently selected from hydrogen (—H), hydroxyl (—OH), halo (e.g. —Cl) and sulphonate (—$SO_{3-}$) groups, with the proviso that at least two of $R_1$ to $R_1$ are sulphonate groups.

An example of a dye useful herein is FD&C Blue #1, also known as Brilliant Blue FCF (Blue 1) as well as other commercial names, which corresponds to general formula (1), wherein $R_2$ is —H and $R_1$, $R_3$, and $R_4$ are sulphonate groups. FD&C Blue #1 is a colorant for foods and other substances to induce a color change. It is denoted by E number E133 and has a color index of 42090. It has the appearance of a reddish-blue powder. It is soluble in water, and the solution has a maximum absorption at about 628 nanometers. It is a synthetic dye produced using aromatic hydrocarbons from petroleum. It is usually a disodium salt. The diammonium salt has CAS number [2650-18-2]. Calcium and potassium salts are also known. Other dyes include red dyes such as FD&C Red #33, FD&C Red #40, and the like; yellow dyes such as FD&C Yellow #5, FD&C Yellow #46, FD&C Yellow #15, and the like; green dyes such as FD&C Green #3; as well as other color dyes and mixtures of any two or more dyes.

In some embodiments the amount of silica sol-gel/dye material in the oral composition is from 0.01 to 0.3%, more particularly from 0.02 to 0.1%, and more particularly from 0.03 to 0.08% by weight. The silica sol-gel/dye material may be spread throughout the composition or, it may be dispersed in a second phase such as a stripe or other coextntded second phase. Such "dual phase" compositions have the advantage that the phases may be differently colored, presenting a more visually attractive product to the consumer Water Water may also be present in the oral compositions of the invention. Water, employed, in the preparation of commercial oral compositions should be deionized and free of organic impurities. Water commonly makes up the balance of the compositions and includes about 0.4% to about 90%, about 10% to about 80% or about 20% to about 70%, or about 30% to about 60% by weight of the oral compositions. This amount of water includes the free water which is added plus that amount which is introduced with other materials such as with sorbitol or any components of the invention. Water can be present in the film flakes, orally acceptable carrier vehicle, or both.

Humectants

Within certain embodiments of the oral compositions, it is also desirable to incorporate a humectant to prevent the composition from hardening upon exposure to air. Certain humectants can also impart desirable sweetness or flavor to dentifrice compositions. The humectant, on a pure humectant basis, generally includes about 15% to about 70% in one embodiment or about 30% to about 65% in another embodiment by weight of the dentifrice composition. Suitable humectants include edible polyhyddc alcohols such as glycerine, sorbitol, xylitol, propylene glycol as well as other polyols and mixtures of these humectants. Nftxtures of glycerine and sorbitol may be used in certain embodiments as the humectant component of the toothpaste compositions herein. The humectant can be present in the film flakes, orally acceptable carrier vehicle, or both.

Orally Acceptable Carrier Vehicle

The oral care compositions of the invention include a vehicle or base into which the film flakes are incorporated. Examples of orally acceptable carrier vehicles include carrier polymers, humectants, water, abrasives, foaming agents, anti-calculus agents, thickener silicas, and the like, or any combination Of two or more thereof. The term "orally-acceptable" refers to a polymer or ingredient which can be used to apply to the oral cavity in a safe manner during normal use.

Carrier Polymers

Carrier polymers can comprise one or more anionic or nonionic polymers, and also may include additional polymers to adjust the viscosity of the formulation or enhance the solubility of other ingredients.

Suitable carrier polymers include polyethylene glycols, polysaccharides (e.g., cellulose derivatives, for example carboxymethyl cellulose, or polysaccharide gums, for example xanthan gum or carrageenan gum). Acidic polymers, for example polyacrylate gels, may be provided in the form of their free acids or partially or fully neutralized water soluble alkali metal (e.g., potassium and sodium) or ammonium salts. Anionic polymers useful herein may enhance the effect of the water insoluble whitening complex, for example in an amount of from about 0.001 to about 5%, more particularly about 0.01 to 5%, more particularly about 0.05 to 4%, more particularly about. 0.05 to 3% of the composition. Such agents are known generally for use in dentifrice, although not for this particular application, useful in the present invention are disclosed in U.S. Pat. Nos. 5,188,821 and 5,192,531; and include synthetic anionic polymeric polycarboxylates, such as 1:4 to 4:1 copolymers of maleic anhydride or acid with another polymerizable ethylenically unsaturated monomer, preferably methyl vinyl ether/maleic anhydride having a molecular weight (M.W.) of about 30,000 to about 1,000,000, most preferably about 300,000 to about 800,000. These copolymers are available for example as Gantrez®, e.g., AN 139 (M.W. 500,000), AN 119 (M.W. 250,000) and preferably S-97 Pharmaceutical Grade (M.W.

700,000) available from ISP Technologies, Inc., Bound Brook, N.J. 08805. Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W: 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone. Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility. A further class of polymeric agents includes a composition containing, homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of about 1,000 to about 2,000,000, described in U.S. Pat. No. 4,842,847, Jun. 27, 1989 to Zahid, incorporated herein by reference. Another useful class of polymeric agents includes polyamino acids containing proportions of anionic surface-active amino acids such as aspartic acid, glutamic acid and phosphoserine, (in addition to the basic amino acid polymers), e.g. as disclosed in U.S. Pat. No. 4,866,161 Sikes et al., incorporated herein by reference.

In preparing oral care compositions, it is sometimes necessary to add some thickening material to provide a desirable consistency or to stabilize or enhance the performance of the formulation. In certain embodiments, the thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Hydroxyalkyl methyl cellulose may also be present in the non-film portion of the oral composition. Natural gums such as karaya, gum arabic, and gum tragacanth can also be incorporated. Colloidal magnesium aluminum silicate or finely divided silica can be used as component of the thickening composition to further improve the composition's texture. In certain embodiments, thickening agents in an amount of about 0.05% to 5%, more particularly about 0.5 to 5% by weight of the total composition are used. Orally acceptable carrier polymers for use in the invention are typically water soluble. Suitable orally acceptable earner polymers for use in the invention will generally dissolve or disperse in water at a temperature of 25° C.

The amount of orally acceptable carrier vehicle polymer in compositions of the invention, whether enhancers, deposition aids, thickeners or the like, or of a combination thereof, suitably ranges from about 0.001 to 10%, more particularly about 0.005 to 5%, more particularly about 1 to 5%, and more particularly about 1 to 3%.

Abrasives

The compositions of the inv enti on, e.g. Composition 1 et seq. may comprise a calcium phosphate abrasive, e.g., tricalcium phosphate (Ca3(PO4)2), hydroxyapatite (Ca10 (PO4)6(OH)2), or dicalcium phosphate dihydrate (CaHPO4.2H2O, also sometimes referred to herein as DiCal) or calcium pyrophosphate. The compositions may include one or more additional abrasives, for example silica abrasives such as precipitated silicas having a mean particle size of up to about 20 microns, such as Zeodent 115®, marketed by J. M. Huber. Other useful abrasives also include sodium metaphosphate, potassium metaphosphate, aluminum silicate, calcined alumina, bentonite or other siliceous materials, or combinations thereof. The silica abrasive polishing materials useful herein, as well as the other abrasives, generally have an average particle size ranging between about 0.1 and about 30 microns, about between 5 and about 15 microns. The silica abrasives can be from precipitated silica or silica gels, such as the silica xerogels described in U.S. Pat. No. 3,538,230, to Pader et at and U.S. Pat. No. 3,862,307, to Digiulio, both incorporated herein by reference. Particular silica xerogels are marketed under the trade name Syloid® by the W. R. Grace & Co., Davison Chemical Division. The precipitated silica materials include those marketed by the J. M. Huber Corp. under the trade name Zeodent®, including the silica carrying the designation Zeodent 115 and 119. These silica abrasives are described in U.S. Pat. No. 4,340,583, to Wason, incorporated herein by reference. In certain embodiments, abrasive materials useful in the practice of the oral care compositions in accordance with the invention include silica gels and precipitated amorphous silica having an oil absorption value of less than about 100 cc/100 g silica and in the range of about 45 cc/100 g to about 70 cc/100 g silica. Oil absorption values are measured using the ASTA Rub-Out Method D281. In certain embodiments, the silicas are colloidal particles having an average particle size of about 3 microns to about 12 microns, and about 5 to about 10 microns. Low oil absorption silica abrasives particularly useful in the practice of the invention are marketed under the trade designation Sylodent XWA® by Davison Chemical Division of W.R. Grace & Co., Baltimore, Md. 21203, Sylodent 650 XWA®, a silica hydrogel composed of particles of colloidal silica having a water content of 29% by weight averaging about 7 to about 10 microns in diameter, and an oil absorption of less than about 70 cc/100 g of silica is an example of a low oil absorption silica abrasive useful in the practice of the present invention. The abrasive is present in the oral care composition of the present invention at a concentration of about 10 to about 60% by weight, in other embodiment about 20 to about 45% by weight, and in another embodiment about 30 to about 50% by weight.

Product Form

Examples of suitable product forms for compositions of the invention include dentifrices, mouthwashes, chewing gums and lozenges.

A type of product form of the present invention is a dentifrice. The term "dentifrice" generally denotes formulations which are used to clean the surfaces of the oral cavity. The dentifrice, is an oral composition that is not intentionally swallowed for purposes of systemic administration of therapeutic agents, but is applied to the oral cavity, used to treat the oral cavity and then expectorated. Typically the dentifrice is used in conjunction with a cleaning implement such as a toothbrush, usually by applying it to the bristles of the toothbrush and then brushing the accessible surfaces of the oral cavity. Preferably the dentifrice is in the form of a paste or a gel (or a combination thereof).

Active Agents

The effective concentration of the active ingredients for optional use herein will depend on the particular agent and the delivery system used. It is understood that a toothpaste for example will typically be diluted with water upon use, while a mouth rinse typically will not be. Thus, an effective concentration of active in a toothpaste will ordinarily be 5-15× higher than required for a mouth rinse. The concentration will also depend on the exact salt or polymer selected. For example, where the active agent is provided in salt form, the counterion will affect the weight of the salt, so that if the counterion is heavier, more salt by weight will be required to provide the same concentration of active ion in the final product. Active agents can include one or more of a fluoride ion source, an anti-calculus agent, an amino acid, a whitening agent, an antibacterial agent, and the like.

Arginine, where present, may be present at levels from e.g., about 0.1 to about 20 wt * (expressed as weight of free base), e.g., about 0.1 to about 3 wt % for a mouthrinse, about 1 to about 10 wt % for a consumer toothpaste or about 7 to about 20 wt % for a professional or prescription treatment product. Fluoride where present may be present at levels of e.g., about 25 to about 25,000 ppm, for example about 25 to about 250 ppm for a mouthrinse, about 750 to about 2,000 ppm for a consumer toothpaste, or about 2,000 to about 25,000 ppm for a professional or prescription treatment product.

Antibacterial agents may be included in the oral composition of the present invention and particularly noncationic halogenated diphenyl ethers agents which are desirable from considerations of effectiveness and safety such as 2',4,4' trichloro-2 hydroxy-diphenyl ether (Triclosan) and 2,2'-dihydroxy-5,5' dibromophenyl ether. The antibacterial agent, when present in the oral composition is present in concentrations of about 0.05 to about 2% by weight and preferably 0.1 to about 1% by weight, Levels of antibacterial agents will vary similarly, with levels used in toothpaste being e.g., about 5 to about 15 times greater than used in mouthrinse. For example, a triclosan mouthrinse may contain, e.g., about 0.03 wt % triclosan while a triclosan toothpaste may contain about 0.3 wt % triclosan.

Agents used to diminish teeth sensitivity such as potassium chloride, potassium nitrate and potassium citrate may also be included in oral compositions of the present invention at concentrations of about 0.1 to about 10% by weight.

Whitening Agents

Whitening agents which may be present in the oral composition include peroxides, metal chlorites, perborates, percarbonates, peroxyacids, persulfates, and combinations thereof. Suitable peroxide compounds include hydrogen peroxide, urea peroxide, calcium peroxide, and mixtures thereof. Suitable metal chlorites include calcium chlorite, barium chlorite, magnesium chlorite, lithium chlorite, sodium chlorite, and potassium chlorite.

Fluoride Ion Source

The oral care compositions may further include one or more fluoride ion sources, e.g., soluble fluoride salts. A wide variety of fluoride ion-yielding, materials can be employed as sources of soluble fluoride in the present, compositions. Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al., incorporated herein by reference. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof. In certain embodiments, the oral care composition of the invention may also contain a source of fluoride ions or fluorine-providing ingredient in amounts sufficient to supply about 25 ppm to about 25,000 ppm of fluoride ions, generally at least about 500 ppm, e.g., about 500 to about 2000 ppm, e.g., about 1000 to about 1600 ppm, e.g., about 1450 ppm. The appropriate level of fluoride will depend on the particular application. A toothpaste for general consumer use would typically have about 1000 to about 1500 ppm, with pediatric toothpaste having somewhat less. A dentifrice or coating for professional application could have as much as about 5,000 or even about 25,000 ppm fluoride. Fluoride ion sources may be added to the compositions of the invention at a level of about 0.01 wt. % to about 10 wt. % in one embodiment or about 0.03 wt. % to about 5 wt. %, and in another embodiment about 0.1 wt. % to about 1 wt. % by weight of the composition in another embodiment. Weights of fluoride salts to provide the appropriate level of fluoride ion will obviously vary based on the weight of the counter ion in the salt.

Foaming Agents

The oral care compositions of the invention also may include an agent to increase the amount of foam that is produced when the oral cavity is brushed. Illustrative examples of agents that increase the amount of foam include, but are not limited to polyoxyethylene and certain polymers including, but not limited to alginate polymers. The polyoxyethylene may increase the amount of foam and the thickness of the foam generated by the oral care carrier component of the present invention. Polyoxyethylene is also commonly known as polyethylene glycol ("PEG") or polyethylene oxide. The polyoxyethylenes suitable for this invention will have a molecular weight of about 200,000 to about 7,000,000. In one embodiment the molecular weight will be about 600,000 to about 2.000,000 and in another embodiment about 800,000 to about 1,000,000. Polyox® is the trade name for the high molecular weight polyoxyethylene produced by Union Carbide. The polyoxyethylene may be present in an amount of about 1% to about 90%, in one embodiment about 5% to about 50% and in another embodiment about 10% to about 20% by weight of the oral care carrier component of the oral care compositions of the present invention. The dosage of foaming agent in the oral care composition (i.e., a single dose) is about 0.01 to about 0.9% by weight, about 0.05 to about 0.5% by weight, and in another embodiment about 0.1 to about 0.2 by weight.

Anticalculus Agents

The oral composition can include at least one anti-calculus composition, such as one or more of the anti-calculus compositions recited in U.S. Pat. No. 5,292,526 titled "Antibacterial Anti-plaque Anticalculus Oral Composition," which is incorporated herein by reference. In various embodiments, the anti-calculus composition includes one or more polyphosphates. The anti-calculus composition can include at least one wholly or partially neutralized alkali metal or ammonium tripolyphosphate or hexametaphosphate salt present in the oral composition at an effective anti-calculus amount. The anti-calculus composition can also include at least one water soluble, linear, molecularly dehydrated polyphosphate salt effective in an anticalculus amount. The anti-calculus composition can also include a mixture of potassium and sodium salts at least one of which is present in an effective anti-calculus amount as a polyphosphate anti-calculus agent. The anti-calculus composition can also contain an effective anticalculus amount of linear molecularly dehydrated polyphosphate salt anti-calculus agent present in a mixture of sodium and potassium salts. Other useful anticalculus agents include polycarboxylate polymers and polyvinyl methyl ether/maleic anhydride (PVME/MA) copolymers, such as GANTREZ®.

Surfactants

The compositions useful in the invention may contain anionic and/or nonioinic surfactants, for example:

i. water-soluble salts of higher fatty acid monoglyceride monosulfates, such as the sodium salt of the monosulfated monoglyceride of hydrogenated coconut oil fatty acids such as sodium N-methyl N-cocoyl taurate, sodium cocomonoglyceride sulfate, ii. higher alkyl sulfates, such as sodium lauryl sulfate, iii. higher alkyl-ether sulfates, e.g., of formula $CH_3(CH_2)_mCH_2(OCH_2CH_2)_nOSO_3X$, wherein m is 6-16, e.g., 10, n is 1-6, e.g., 2, 3 or 4, and X is Na or K, for example sodium laureth-2 sulfate $(CH_3(CH_2)10CH_2(OCH_2CH_2)_2OSO_3Na)$.

iv. higher alkyl aryl sulfonates such as sodium dodecyl benzene sulfonate (sodium lauryl benzene sulfonate)

v. higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate.

By "higher alkyl" is meant, e.g., C6-30 alkyl. In particular embodiments, the anionic surfactant is selected from sodium lauryl sulfate and sodium ether lauryl sulfate. The anionic surfactant may be present in an amount which is effective, e.g., >0.01% by weight of the formulation, but not at a concentration which would be irritating to the oral tissue, e.g., <10%, and optimal concentrations depend on the particular formulation and the particular surfactant. For example, concentrations used for a mouthwash are typically on the order of one tenth that used for a toothpaste. In one embodiment, the anionic surfactant is present in a toothpaste at from about 0.3% to about 4.5% by weight, e.g., about 1.5%.

Nonionic surfiictants include nonan ionic polyoxyethylene surfactants such as Polyoxamer 407, Steareth 30, Polysorbate 20, and PEG-40 castor oil and amphoteric surfactants such as cocamiopropyl betaine (tegobaine) and cocamidopropyl betaine lauryl glucoside condensation products of ethylene oxide with various hydrogen containing, compounds that are reactive therewith and have long hydorphobic chains (e.g., aliphatic chains of about 12 to 20 carbon atoms), which condensation products ("ethoxamers") contain hydrophilic polyoxyethylene moieties, such as condensation products of poly (ethylene oxide) with fatty acids, fatty alcohols, fatty amides and other fatty moieties, and with propylene oxide and polypropylene oxides (e.g., Pluronic®.materials).

The compositions of the invention may optionally contain mixtures of surfactants e.g., comprising anionic surfactants and other surfactants that may be anionic, cationic, zwitterionic or nonionic. Generally, surfactants are those which are reasonably stable throughout a wide pH range. Surfactants are described more fully, for example, in U.S. Pat. No. 3,959,458, to Agricola et al.; U.S. Pat. No. 3,937,807, to Haefele; and U.S. Pat. No. 4,051,234, to Gieske et al., which are incorporated herein by reference. In certain embodiments, the anionic surfactants useful herein include the water-soluble salts of alkyl sulfates having about 10 to about 18 carbon atoms in the alkyl radical and the water-soluble salts of sulfonated monoglycerides of fatty acids having about 10 to about 18 carbon atoms. Sodium lauryl sulfate, sodium lauroyl sarcosinate and sodium coconut monoglyceride sulfonates are examples of anionic surfactants of this type. In a particular embodiment, the composition of the invention, e.g., Composition 1, et seq., comprises sodium lauryl sulfate.

The surfactant or mixtures of compatible surfactants can be present in the compositions of the present invention in about 0.1% to about 5.0%, in another embodiment about 0.3% to about 3.0% and in another embodiment about 0.5% to about 2.0% by weight of the total composition.

Flavoring Agents

The oral care compositions of the invention may also include a flavoring agent. Flavoring agents which are used in the practice of the present invention include, but are not limited to, essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint. The flavoring agent may be incorporated in the oral composition at a concentration of about 0.1 to about 5% by weight and about 0.5 to about 1.5% by weight. The dosage of flavoring agent in the individual oral care composition dosage (i.e., a single dose) is about 0.001 to 0.05% by weight and in another embodiment about 0.005 to about 0.015% by weight.

Other Optional Ingredients

In addition to the above-described components, the embodiments of this invention can contain a variety of optional dentifrice ingredients some of which are described below. Optional ingredients include, for example, but are not limited to, adhesives, sudsing agents, sweetening agents, and additional coloring agents. These and other optional components are further described in U.S. Pat. No. 5,004,597, to Majeti; U.S. Pat. No. 3,959,458 to Agricola et al. and U.S. Pat. No. 3,937,807, to Haefele, all being incorporated herein by reference.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

In general, the various agents and materials described herein, e.g., fluoride ion source, antibacterials, flavoring agents, whitening agents, and the like, can be present in the film flakes, orally acceptable carrier vehicle, or both.

Unless otherwise specified, all percentages and amounts expressed herein and elsewhere in the specification should be understood to refer to percentages by weight. The amounts given are based on the active weight of the material. For convenience, components of the composition of invention are expressed in the singular; however it is to be understood that mixtures of components are encompassed b use of the singular expression, for example, "an orally acceptable carrier polymer" may include mixtures of two or more polymers described herein. Some embodiments of the present invention provide an oral care composition (Composition 1) comprising:

(i) flakes of a water dissolvable or soluble film comprised of
   (a) a water soluble cellulose polymer in the form of a polymer matrix, and
   (b) a silica sol-gel/dye material entrained in the polymer matrix, and, optionally, other actives, and
(ii) an orally acceptable carrier vehicle,
wherein the film is pliable, for example:
   1.1. Composition 1 wherein the cellulose polymer comprises cellulose ethers, e.g., selected from
      (i) alkylcellulose, methylcellulose;
      (ii) hydroxy alkyl cellulose, e.g., selected from hydroxypropyl methyl cellulose, hydroxyethylpropyl cellulose, hydroxybutyl methyl cellulose, hydroxy propyl methyl cellulose, carboxymethyl cellulose and mixtures thereof;
      and (iii) mixtures thereof;
   1.2. Any of the foregoing compositions wherein the film comprises a starch, e.g. a pregelatinized starch;
   1.3. Any of the foregoing compositions wherein the film comprises a plasticizer, e.g, a polyalcohol, e.g., sorbitol, propylene glycol, glycerol, or low molecular weight polyethylene glycol, e.g., PEG 200;
   1.4. Any of the foregoing compositions wherein the film comprises propylene glycol, e.g., in an amount effective to provide plasticity to the film, e.g., about 20-30% by dry weight of the film;
   1.5. Any of the foregoing compositions wherein the film comprises betaine, e.g., in an amount effective to provide a pliable film, e.g., about 1-5% by dry weight of the film;
   1.6. Composition 1 wherein the cellulose polymer is hydroxypropylmethyl cellulose.
   1.7. Any of the foregoing compositions wherein the film does not contain a polymer that functions as a mucoadhesive polymer, e.g., polymers containing acrylate repeating units.
   1.8. Any of the foregoing compositions wherein the film does not contain starch.
   1.9. Any of the foregoing compositions wherein the dye is an anionic triphenylmethane the e.g., diaminotriphenylmethane dyes containing from two to four sulphonate groups, such as FD&C. Blue #1;
   1.10. Any of the foregoing compositions wherein the film is substantially dissolved after a period of greater than 30 seconds and less than 180 seconds of brushing, scrubbing or agitation in the oral cavity or on the skin in the presence of water;
   1.11. Any of the foregoing compositions wherein the average thickness of the film is 1-10 mil, e.g. 1.5-3 mil, e.g. about 1.5 mil about 2 mil or about 3 mil;
   1.12. Any of the foregoing compositions wherein the film comprises, by dry weight of the film, 20-60% hydroxypropylmethyl cellulose; 10-30% propylene glycol; 1-5% betaine; and 15-30 or 15-55% silica sol-gel/dye material;
   1.13. Any of the foregoing compositions wherein the film additionally comprises flavors, fragrances, antibacterial agents, anesthetic agents or combinations thereof;
   1.14. Any of the foregoing compositions wherein the films flakes have a particle size of 10-100 mesh or 20-60 mesh or 30-50 mesh;
   1.15. Any of the foregoing compositions wherein the film is in an orally acceptable carrier vehicle which comprises a synthetic anionic polymeric polycarboxylate;
   1.16. Any of the foregoing, compositions wherein the orally acceptable carrier vehicle is a 1:4 to 4:1 copolymers of maleic anhydride or acid with another polymerizable ethylenically unsaturated monomer;
   1.17. Any of the foregoing compositions wherein the film is in an orally acceptable carrier vehicle wherein the orally acceptable carrier vehicle comprises a methyl vinyl ether/maleic anhydride copolymer having an average molecular weight (M.W.) of about 30,000 to about 1,000,000, e.g. about 300,000 to about 800,000;
   1.18. Any of the foregoing compositions wherein the film is in an orally acceptable carrier vehicle wherein the orally acceptable carrier vehicle comprises about 1-5%, e.g., about 2% of the weight of the total composition;
   1.19. Any of the foregoing, compositions further comprising an effective amount of fluoride, e.g., wherein the fluoride is a salt selected from stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and combinations thereof;
   1.20. Any of the foregoing compositions comprising L-arginine in free or orally acceptable salt form;
   1.21. Any of the foregoing compositions comprising buffering agents, e.g., sodium phosphate buffer (e.g., sodium phosphate monobasic and disodium phosphate)
   1.22. Any of the foregoing compositions comprising an additional humectant, e.g., selected from, sorbitol, propylene glycol, polyethylene glycol, xylitol, and mixtures thereof;
   1.23. Any of the foregoing compositions further comprising an abrasive or particulate;
   1.24. The foregoing composition wherein the abrasive or particulate is selected from sodium bicarbonate, calcium phosphate (e.g., dicalcium phosphate dihydrate), calcium sulfate, precipitated calcium carbonate, silica (e.g., hydrated silica), iron oxide, aluminum oxide, perlite, plastic particles, e.g., polyethylene, and combinations thereof;
   1.25. Any of the foregoing compositions comprising an abrasive in an amount of about 15 wt. % to about 70 wt. of the total composition weight;
   1.26. Any of the foregoing compositions comprising one or more surfactants, e.g., selected from anionic, cationic, zwitterionic, and nonionic surfactants, and mixtures thereof e.g., comprising an anionic surfactant, e.g., a surfactant selected from sodium lauryl sulfate, sodium ether lauryl sulfate, and mixtures thereof, e.g. in an amount of from about 0.3% to about 4.5% by weight;
   1.27. Any of the foregoing compositions further comprising a viscosity modifying, amount of one or more polymers selected from polyethylene glycols, polysaccharides (e.g., cellulose derivatives, for example carboxymethyl cellulose, polysaccharide gums, for example xanthan gum or carrageenan gum), and combinations thereof;
   1.28. Any of the foregoing compositions comprising one or more antibacterial agents, for example comprising, an antibacterial agent selected from halogenated diphenyl ether (e.g. triclosan), herbal extracts and essential oils (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, zinc, citrate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing; e.g., comprising triclosan or cetylpyridinium chloride;

1.29. Any of the foregoing compositions comprising a whitening agent, e.g., a selected from the group consisting of peroxides, metal chlorites, perborates, percarbonates, peroxyacids, hypochlorites, and combinations thereof;

1.30. Any of the foregoing compositions further comprising hydrogen peroxide or a hydrogen peroxide source, e.g., urea peroxide or a peroxide salt or complex (e.g., such as peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate);

1.31 Any of the foregoing compositions farther comprising a source of calcium and phosphate selected from (i) calcium-glass complexes, e.g., calcium sodium phosphosilicates, and (ii) calcium-protein complexes, e.g., casein phosphopeptide-amorphous calcium phosphate;

1.32. Any of the foregoing compositions further comprising a soluble calcium salt, e.g., selected from calcium sulfate, calcium chloride, calcium nitrate, calcium acetate, calcium lactate, and combinations thereof;

1.33. Any of the foregoing compositions further composing a physiologically or orally acceptable potassium salt, e.g., potassium nitrate or potassium chloride, in an amount effective to reduce dentinal sensitivity;

1.34. Any of the foregoing compositions in the form of a dentifrice, for example a toothpaste, e.g., a clear gel or opaque toothpaste;

1.35. Any of the foregoing compositions in the form of a clear gel or opaque toothpaste and the dye is released upon dissolution of the film thereby changing the color of the toothpaste after brushing for a period of 30-180 seconds, e.g., about 45-60 seconds in a toothpaste for use by a child or about 90-120 seconds in a toothpaste for use by an adult, thereby releasing the dye and providing a color signal to the user of adequate brushing;

The invention further provides a method of cleaning the teeth comprising brushing with a toothpaste comprising an orally acceptable dissolvable film of a cellulose polymer and having entrained therein a silica sol-gel/dye material (e.g., Composition 1 et seq.), wherein brushing is continued until the film disintegrates and the dye provides a color signal to the user of adequate brushing, for example, wherein, the brushing time before the film matrix dissolves is between 30 and 180 seconds, e.g., about 45-60 seconds for a toothpaste for use by a child and about 90-120 seconds for a toothpaste for use by an adult.

In some embodiments, the composition is a clear gel toothpaste; wherein the dye is released from the first film after brushing for a period of 30 to 120 seconds. In some embodiments, the dye is released from the first film after brushing for a period of 60 seconds. In some embodiments, the dye is released from the first film after brushing for a period of 90 seconds. In some embodiments, the dye is released from the first film after brushing for a period of 120 seconds.

The invention further provides a method of cleaning the teeth, removing plaque, treating, halitosis, or treating gingivitis comprising brushing the teeth with Composition 1, et seq.

In some embodiments, the film is substantially dissolved after a period of greater than 30 seconds and less than 180 seconds of brushing scrubbing or agitation in the presence of water.

In some embodiments, substantially all of the dye is released from the film at the same point in time.

In some embodiments the composition is stable, i.e., no visible dye is observed in the carrier vehicle, for a period of 1 month or 2 months, or 3 months, or 6 months, or 1 year or 2 years upon storage at about room temperature.

Yet other embodiments provide a method of cleaning the teeth comprising brushing with a toothpaste according to Composition 1 et seq., wherein brushing is continued until the film releases substantially all of the dye; thereby providing a color signal to the user of adequate brushing.

In some embodiments, substantially all of the dye is released at one time. As used herein, the term "substantially all" refers to greater than 90% of the total amount of dye contained in the film.

In another embodiment is provided a method for providing storage stability to a dentifrice containing; dye comprising entrapping said dye in a silica sol-gel and incorporating said entrapped dye in a film comprised of a cellulose polymer and incorporating said film, into an orally acceptable carrier vehicle.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight.

EXAMPLE

Example 1

Film making Procedure.

Approximately fifty percent of the required film formula water is weighed out and heated as necessary depending, on the polymer type. Polymers (HPMC, MC, etc) are slowly added to the water under mixing conditions and the polymers are allowed to disperse and hydrate for 10-15 minutes. Additional water up to the full amount is added until the slurry has the consistency of honey. Plasticizers and surfactants should then be added while mixing and allowed to mix for 5 minutes. Other particles such as dyes, etc should then be added to the mixture and allowed to mix for 10 additional minutes. The slurry should then be de-aerated. Films can then be cast and dried from the slurry to the desired thickness typically 1-10 mils.

Films are made from the ingredients in Table 1 and evaluated for pliability. Film pliability is an important aspect of film making as it dictates the feasibility of manufacture. Films that lack pliability will crack during drying resulting in a material that cannot be handles easily and thus cannot be manufactured. Pliability is easy to assess by taking a piece of film a minimum of 3 inches square and tugging and folding the film. Pliable films will not easily tear nor crack during this manipulation.

TABLE 1

| Ingredient | Standard Pigment Film | Dye Containing Film | Dye Containing Film |
|---|---|---|---|
| HPMC E5 | 55.20% | 18% | 18% |
| HPMC E50 | 0% | 18% | 18% |
| Blue 15 | 16.90% | 0% | 0% |
| FD&C Blue #1 entrapped in a silica sol-gel matrix | 0.00% | 21% | 21% |
| Red 30 | 3.40% | 0 | 0 |
| Propylene Glycol | 20.7 | 21% | 21% |
| Tween 80 | 3.8 | 0 | 3.8 |
| Betaine | 0 | 3.3 | 0 |
| Pliable | yes | yes | no |

An experiment is carried to evaluate the ability of the films to retain dye. Film stability is determined by measuring the degree of color bleeding using a spectrophotometer which can measure on the L, a, b scale. Films are loaded into a gel toothpaste where there is higher clarity and high water mobility and permitted to age at room temperature for a minimum of 24 hours and up to 3 months. Films can be filtered out of the gel prior to color evaluation. As noted in the Table 2 there is a minimal change in any of the measured color parameters indicating that the films are stable and exhibit minimal bleeding.

TABLE 2

|  | L* | a* | b* |
|---|---|---|---|
| Initial | 96.08 | −0.23 | 0.63 |
| 3 Month | 95.24 | −1.38 | 0.17 |

The invention claimed is:

1. An oral care composition comprising:
   (i) flakes of a water dissolvable or soluble film comprising:
      (a) about 15 to about 40% by weight of a water soluble cellulose polymer in the form of a polymer matrix, wherein the cellulose polymer is hydroxypropylmethyl cellulose; and
      (b) a dye which is entrapped in a silica sol-gel, wherein the silica sol-gel is entrained in the polymer matrix, and
      (c) betaine; and
   (ii) an orally acceptable carrier vehicle,
   wherein the film flakes are single-layer film flakes and are pliable;
   wherein the hydroxypropylmethyl cellulose is a blend of a first hydroxypropylmethyl cellulose having a viscostity ranging from 4 to 6 mPas, and a second hydroxypropylmethyl cellulose having a viscosity ranging from 40 cps to 60 mPas; and
   wherein the first and second hydroxylpropylmethyl cellulose are present in a weight ratio of about 1:1.

2. The composition of claim 1, wherein the cellulose polymer further comprises one or more of hydroxyethylpropyl cellulose, hydroxybutyl methyl cellulose, carboxymethyl cellulose and mixtures thereof.

3. The composition according to claim 1, wherein the film further comprises a plasticizer selected from sorbitol, propylene glycol, glycerol, and polyethylene glycol.

4. The composition according to claim 1, wherein the film is dissolved after a period of greater than 30 seconds and less than 180 seconds of brushing, scrubbing or agitation in the presence of water.

5. The composition according to claim 1 wherein the average thickness of the film is 1.5-3 mil.

6. The composition according to claim 1 wherein the dye is FD&C Blue#1.

7. The composition according to claim 1, comprising, by dry weight of the film, 10-30% propylene glycol; 1-5% betaine; and 15-30% dye entrapped silica sol-gel.

8. The composition according to claim 1 which is stable upon storage at about room temperature for 1 month, 2 months, 3 months, 6 months, 1 year or 2 years.

9. The composition according to claim 1, which is a clear gel toothpaste; wherein the dye is released from said film after brushing for a period of 30 to 120 seconds.

10. A method of cleaning the teeth comprising brushing the teeth with a composition according to claim 1, wherein brushing is continued until the film releases all of the dye; thereby providing a color signal to the user of adequate brushing.

11. The composition according to claim 1, wherein composition does not contain polysorbate 80.

12. The compositition according to claim 1, wherein the film flakes have a particle size of about 10 to about 100 mesh.

13. The compositition according to claim 1, wherein the film flakes have a particle size of about 20 to about 60 mesh.

14. The compositition according to claim 1, wherein the film flakes have a particle size of about 30 to about 50 mesh.

15. An oral care composition comprising:
   (i) flakes of a water dissolvable or soluble film comprising:
      (a) a polymer matrix comprising a water soluble cellulose polymer that is present in an amount ranging from about 15 wt. % to about 40 wt. % based on the total weight of the oral care composition, the cellulose polymer comprising a blend of:
         a first hydroxypropylmethyl cellulose having a viscostity ranging from 4 to 6 mPas, and
         a second hydroxypropylmethyl cellulose having a viscosity ranging from 40 cps to 60 mPas; and
      (b) a dye which is entrapped in a silica sol-gel, wherein the silica sol-gel is entrained in the polymer matrix, wherein the dye-entrapped silica sol-gel is present in an amount ranging from about 15 wt. % to about 30 wt. % based on the total weight of the oral care composition and the dye is FD&C Blue#1; and
      (c) betaine present in an amount ranging from about 1 wt. % to about 5 wt. % based on the total weight of the oral care composition; and
   (ii) an orally acceptable carrier vehicle,
   wherein the film flakes have a particle size of about 30 to about 50 mesh;
   wherein the first hydroxypropylmethyl celluose and the second hydroxypropylmethyl cellulose are present in a weight ratio of about 1:1.

* * * * *